(12) United States Patent
Hill et al.

(10) Patent No.: US 7,957,504 B2
(45) Date of Patent: Jun. 7, 2011

(54) METHOD AND APPARATUS FOR MEASURING ENRICHMENT OF UF6

(75) Inventors: Thomas Roy Hill, Santa Fe, NM (US); Kiril Dimitrov Ianakiev, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 102 days.

(21) Appl. No.: 12/582,641

(22) Filed: Oct. 20, 2009

(65) Prior Publication Data

US 2010/0098211 A1    Apr. 22, 2010

Related U.S. Application Data

(60) Provisional application No. 61/106,744, filed on Oct. 20, 2008.

(51) Int. Cl.
*G01N 23/223* (2006.01)
*G01N 23/06* (2006.01)
*G01N 23/04* (2006.01)

(52) U.S. Cl. ............................ 378/45; 378/53; 378/57

(58) Field of Classification Search ............ 378/44, 378/45, 46, 50, 51, 53, 62, 57, 64
See application file for complete search history.

(56) References Cited

U.S. PATENT DOCUMENTS

| | | | | |
|---|---|---|---|---|
| 3,697,235 | A | * | 10/1972 | Ogle, Jr. ................ 423/253 |
| 5,419,820 | A | * | 5/1995 | Horton et al. ............ 204/157.22 |
| 7,081,626 | B2 | | 7/2006 | Ianakiev et al. |

OTHER PUBLICATIONS

Strittmatter, "A Gas Phase Enrichment Monitor," Nuclear Technology vol. 59 (Nov. 1982) pp. 355-362.
Packer et al., "Measurement of the Enrichment of Uranium in the Pipe Work of a Gas Centrifuge Plant," 26th Meeting of the INMM, Albuquerque, NM, Jul. 1985.
Ianakiev et al., "Effect of Temperature on Counting Measurements in a Uranium Enrichment Monitor Based on a NaI(Tl) Spectrometer and Transmission Source," IEEE, NSS-MIC Conference, San Diego, CA, Nov. 2006.
Ianakiev et al., "Improving the Accuracy of a Uranium Enrichment Monitor based on a NaI(Tl) Spectrometer and Transmission Source," 29th ESARDA Meeting, Aix en Provence, France, May 22-24, 2007.

* cited by examiner

*Primary Examiner* — Irakli Kiknadze
(74) *Attorney, Agent, or Firm* — Husch Blackwell LLP; Meredith H. Schoenfeld

(57) ABSTRACT

A system and method are disclosed for determining the enrichment of $^{235}U$ in Uranium Hexafluoride (UF6) utilizing synthesized X-rays which are directed at a container test zone containing a sample of UF6. A detector placed behind the container test zone then detects and counts the X-rays which pass through the container and the UF6. In order to determine the portion of the attenuation due to the UF6 gas alone, this count rate may then be compared to a calibration count rate of X-rays passing through a calibration test zone which contains a vacuum, the test zone having experienced substantially similar environmental conditions as the actual test zone. Alternatively, X-rays of two differing energy levels may be alternately directed at the container, where either the container or the UF6 has a high sensitivity to the difference in the energy levels, and the other having a low sensitivity.

20 Claims, 4 Drawing Sheets

__US 7,957,504 B2__

METHOD AND APPARATUS FOR MEASURING ENRICHMENT OF UF6

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to systems and methods for measuring enrichment of Uranium Hexafluoride (UF6). More specifically, the present invention relates to a system and method for directing ionizing radiation in the form of X-Rays at a radiation pervious chamber containing UF6 to determine the amount of $^{235}$U present relative to the amount of Uranium.

BACKGROUND ART

It has been reported that approximately 99.99% of all natural Uranium on Earth is composed of either $^{235}$U or $^{238}$U, with $^{238}$U comprising 99.28% and $^{235}$U comprising 0.71% of all natural Uranium. However, in order to achieve a nuclear chain reaction capable of sustaining a fission reaction in Uranium, a majority of the neutrons released by a fissioning $^{235}$U atom must impact other $^{235}$U atoms. This requires that the Uranium be enriched such that the percentage of $^{235}$U is between 3-5% to sustain a nuclear fission chain reaction, with weapons grade Uranium requiring much higher concentrations of $^{235}$U. Typically, such enrichment occurs in gaseous diffusion or centrifuge plants, where Uranium in the form of UF6 is enriched to increase the $^{235}$U content. However, when enriching Uranium, it is very important to keep track of the concentration of $^{235}$U in the Uranium sample in order to safeguard the plant and its workers, as well as for quality control purposes and to guard against the production of more enriched, potentially weapons grade, Uranium.

Methods of detecting the amount of $^{235}$U in a sample are well known in the art: $^{235}$U spontaneously radiates 186 keV gamma radiation which can be detected and measured apart from 186 keV background gamma radiation. In order to measure the total Uranium content of a sample, a separate radioactive material source of non-186 keV radiation—typically $^{109}$Cd, $^{241}$Am or $^{57}$Co—is used to irradiate the sample. The count rate of this non-186 keV radiation after being attenuated by a sample container, as well as the count rate of this radiation after being attenuated by the sample container and UF6 in the test sample, allows for the calculation of the enrichment factor of the sample.

Embodiments of the present invention provide for a system in which the energy source is not radioactive and does not decay with time, and where the radiation is emitted from an artificial source preferably utilizing an energetic electron process. It is further desirous that a more accurate enrichment factor is calculable with a lower level of instrument stability and temperature dependence.

BRIEF SUMMARY OF THE INVENTION

One or more of the embodiments of the present invention provide for a system and method for determining the enrichment of Uranium-235 in Uranium Hexafluoride (UF6), though the system and method could be used for determining the isotopic content of other types of samples as well. In one embodiment, a detector counts the number of 186 keV gamma rays, which are spontaneously emitted by $^{235}$U in a sample of UF6 as it decays. An artificial source of X-rays, which preferably utilizes an energetic electron process, is used to direct a collimated beam of X-rays at a container test zone containing the sample of UF6. This beam could be directed to impinge the container test zone at a 90 degree angle to the longitudinal axis of the container test zone, at an acute angle to the longitudinal axis of the test zone, or along the longitudinal axis of the test zone.

The X-ray beam is preferably filtered to contain X-rays of a specific energy level, preferably between 12 keV and 120 keV, and impinges on the container and the UF6, and some of the X-rays are attenuated by the UF6 and/or by the container itself. A low energy (preferably 10 keV to 300 keV) gamma sensitive detector, which may be an NaI(TI) or other type of scintillator, is oriented in the path of the X-ray beam such that the container test zone is between the detector and the artificial X-ray source. A more complex phoswich scintillator may be used for more effective back shielding and active Compton suppression in the energy region of the U-235 gamma rays. The detector then detects and counts the X-rays which pass through the container and the UF6.

In order to determine the portion of the attenuation due to the UF6 and not the container or other hardware, this count rate may then be compared to a calibration count rate of substantially similar X-rays passing through the container test zone or a calibration test zone which contains a vacuum. This calibration count rate would be pre-measured (infrequently in the prior art—on the order of once ever few months to once every few years) on test zones substantially similar to the sample test zone used to contain the UF6. These count rates can then be used, in combination with the count of 186 keV gamma rays emitted spontaneously by the $^{235}$U in the sample to determine the enrichment of the $^{235}$U in the sample. However, geometry, aging or temperature changes between the test zones on which the calibrations were taken and those actually used with the experiments cause significant error.

In a preferred embodiment, the calibration count is taken using a vacuum-containing second calibration test zone positioned adjacent to the UF6-containing first test zone such that the second test zone experiences substantially similar environmental conditions as does the first test zone. Thus, as the second test zone is substantially similar to the first test zone and experiences substantially similar environmental conditions as the first test zone, the number of X-rays it attenuates is substantially similar to the number of X-rays attenuated by the first test one absent a UF6 sample. Additionally, its location adjacent the first test zone allows for the X-ray beam to be directed at both test zones simultaneously, such that a second detector counts the X-rays passing through the second test zone while the first detector counts the X-rays passing through the first test zone and the UF6 sample.

In the alternative, a non-simultaneous count could be taken of the X-rays passing through the test zones, i.e. a count could be taken of the X-rays passing through only one of the test zones, and then a separate count could be taken of the X-rays passing through the other test zone. Thus, the calibration count could be taken simultaneously with, or before or after each run, or every N number of runs, which would reduce the error resulting from environmental changes between the time of calibration and the actual testing.

In another preferred embodiment, when placing a second, vacuum-containing test zone adjacent the UF6-containing test zone is not a viable option, a beam of X-rays is similarly directed at a UF6-containing test zone. However, this X-ray beam is filtered such that the X-rays in the beam have a first energy level for a period of time, and then a second energy for a period of time. This alternation of energy levels may be accomplished with two different filters mounted on a rotational assembly which rotates the filters such that the X-ray beam is alternately filtered by one and then the other. The first and second energy levels are selected such that either Uranium or the test zone container material has a high "sensitivity" to the change in energy levels while the other has a low "sensitivity" to the change. Thus, the attenuation caused by either the Uranium or the test zone container would be significantly different at the first energy level as the second, while the other material attenuates substantially the same amount of X-rays at both energy levels. This allows a differentiation between the X-rays attenuated by the container test zone and those attenuated by the UF6. Thus, this preferred embodiment allows for "re-calibration" when a sample is tested.

In another embodiment, the X-Ray beam is directed though the container test zone at an acute angle α to the longitudinal axis of the container test zone. This allows the X-rays more exposure to the UF6 gas, and more chance for the X-rays to be attenuated.

In another embodiment, the X-ray beam is again directed though the container test zone at an acute angle α to the longitudinal axis of the container test zone. However, the detector, which is preferably a phoswich scintillator is not positioned within the path of the X-ray beam, but is instead disposed along the pipe between the zones of entry and exit of the X-ray beam through the container test zone, and preferably rotated 90 degrees around the longitudinal axis of the test zone from the zones of entry and exit of the X-ray beam. This allows for fluorescent X-rays which are emitted by Uranium atoms when excited by X-rays to be detected by the detector while avoiding the Compton scattering and backscattering caused by the X-ray beam impinging the container walls. The count rate of the fluorescent X-rays emitted by the Uranium can then be used, in combination with the count of 186 keV gamma rays emitted spontaneously by the $^{235}$U in the sample to determine the enrichment of the $^{235}$U in the sample.

BRIEF DESCRIPTION OF THE DRAWINGS

For a better understanding of the present invention, reference may be made to the accompanying drawings in which.

DETAILED DESCRIPTION OF THE INVENTION

Figure 1:
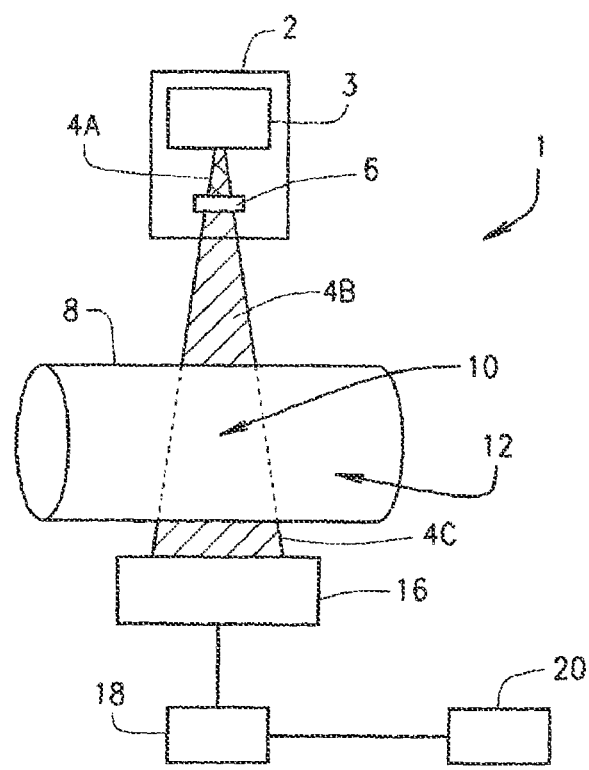
FIG. 1 is a schematic diagram of an embodiment of the present invention for measuring the attenuation of a container which does not contain UF6 gas.

FIG. 1 illustrates a schematic diagram of an embodiment of a system 1 for determining the enrichment factor of $^{235}$U in Uranium Hexafluoride (UF6). An artificial X-ray source 2, which is preferably a 130 kV X-ray source and which can preferably artificially produce and emit X-rays from about 12 keV to about 120 keV, includes an X-ray generation source 3 which emits a collimated beam of X-rays 4, and an X-ray filter 6. The X-ray generator source 3 is a man-made machine which artificially produces X-rays preferably utilizing an energetic electron process. The X-ray generation source 3 generates and emits X-ray radiation as an X-ray beam 4. X-ray beam 4 is divided into several different sections, which are shown as three in number and are labeled 4A, 4B and 4C, each of which designate a portion of X-ray beam 4 with a specific intensity and/or energy level. For example, as X-ray beam 4 is emitted from the X-ray generator source 3, it is labeled X-ray beam 4A. In the illustrated structure it then encounters filter 6, which filters out of X-ray beam 4A X-rays of unwanted energies, such that X-ray beam 4B is emitted from the artificial X-ray source 2. It is noted that the filter 6 need not be included inside the artificial X-ray source 2, but could instead be a separate component. It is further noted that an X-ray generation source 3 capable of emitting X-rays of substantially only those energies desired could be used instead of filter 6. The X-ray beam 4 is preferably a "hard" X-ray beam with energy levels of between 12 keV and 120 keV, which have higher penetrating abilities than lower energy "soft" X-rays. However, "soft" X-rays could be used if less penetrating abilities are needed.

The X-ray beam 4B emitted from the artificial X-ray source 2 is directed at a container 8 with a test zone 10, which is preferably an aluminum alloy pipe (hereinafter "aluminum") which initially holds a vacuum in its interior chamber 12 for the purposes of calculating the attenuation of the container 8 test zone 10 for a given keV. X-ray beam 4B is directed at the test zone 10 where it passes through the test zone 10. However, some of the X-rays interact with the test zone 10 wall, leading to some attenuation of X-ray beam 4B. This attenuated X-ray beam 4C is then detected by a detector 16 capable of measuring the quantity of X-rays passing through the container 8 test zone 10. The detector 16 is preferably a Thallium doped Sodium Iodide scintillating detector. Detector 16 is also operable for counting the amount of background 186 keV radiation.

The detector 16 is connected to a multi-channel analyzer 18 which sorts the pulses generated by the detector 16 when it detects the X-rays. The multi-channel analyzer 18 then creates a histogram of the X-rays energy levels from X-ray beam 4C which were detected by the detector 16, and transmits this information to an output device 20 which is preferably a digital processor such as that in a personal computer. The count rate of the artificial X-ray source 2 having been attenuated by the test zone 10, and which also includes any background radiation, serves as a baseline for future measurements and is abbreviated $I_0(t)$. The count rate of 186 keV background radiation serves as a baseline as well, and is abbreviated B.

Once these baselines have been established, the container 8 test zone 10 is provided with a sample of Uranium Hexafluoride (UF6) 22, which is preferably gaseous (as used hereinafter for convenience) but could be solid or liquid as tested, in its interior chamber 12, as is shown in the system 21 in FIG.

2. The X-ray beam 4B is again directed at the test zone 10 where it passes through the test zone 10, but this time additionally passes through UF6 gas mixture 22 in the interior chamber portion 12 in the test zone 10. Thus, the X-ray beam 4B is attenuated by the container 8 as before, but is additionally attenuated by the UF6 gas mixture 22. This additionally attenuated X-ray beam 4D is then detected by the detector 16 which is capable of measuring the quantity of X-rays passing through the container 9 test zone 10 and the UF6 gas, mixture 22 in the interior chamber 12 of the container 9 test zone 10. Detector 16 is capable of counting gamma rays having an energy level of 186 keV which are emitted by $^{235}$U.

The detector 16 again transmits its detections to the multi-channel analyzer 18 which sorts the pulses generated by the detector 16. The multi-channel analyzer 18 again creates a histogram of the count rate of the X-rays energies which were detected by the detector 16, and transmits this information to the output device 20. This count rate of the X-rays having been attenuated by the test zone 10 of the container 9 and the UF6 22, and which again includes any background radiation, is abbreviated I. The count rate of 186 keV gamma rays, which includes background radiation of this energy level and that emitted spontaneously by $^{235}$U, is abbreviated R. The formula for calculating the enrichment (E) of $^{235}$U in the UF6 is then $E=K*(R-B)/\ln[I-I_0(t)]$, where K is a calibration constant which takes into account different factors of detection efficiency (such as the geometrical orientation of the system, the detection abilities of the scintillator, the multichannel analyzer) of both the transmitted X-rays and the U-235 radiation.

It is noted that hard X-rays, which have an energy level of between 12 keV and 120 keV, pose less of a risk of "pile-up" at the 186 keV energy level than does higher energy electromagnetic radiation, or soft X-rays. It is preferable to use X-ray energy values of less than about 50 keV to further lessen the chances of 186 keV pile-up, unless there is some compensation for such pileup. If there is some compensation for this pile-up, the actual energy level of the X-ray beam 4 may be between 12 keV and 120 keV, so long as it remains constant from the baseline measurements to the actual UF6 measurement. Altering the energy level of the X-ray beam 4 between baseline measurement and the UF6 measurements will affect the accuracy of the Uranium content calculations. Some deviation of the X-ray beam 4 energy level may be acceptable when creating "Go/No-Go" systems when the actual Uranium enrichment is unimportant beyond whether a certain level has been reached.

Figure 3:
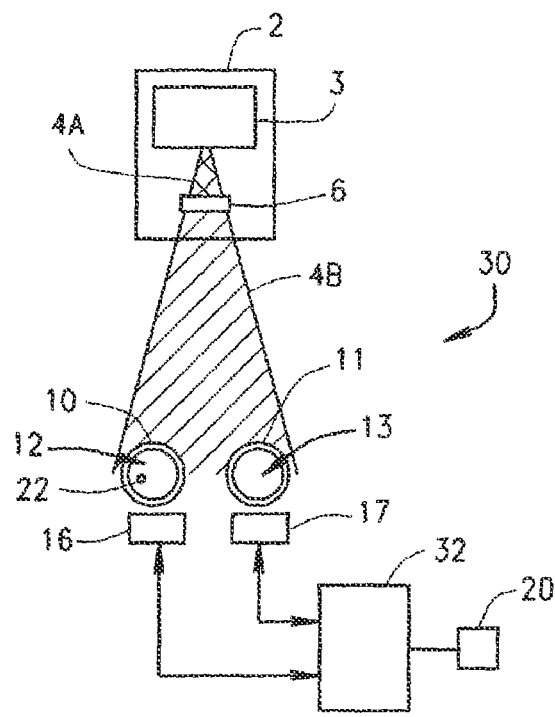
FIG. 3 is a schematic diagram of a preferred embodiment of the present invention including an additional reference pipe.

FIG. 3 illustrates a preferred embodiment of a system 30 for measuring the Uranium enrichment in UF6 gas. As above, an artificial X-ray source 2 emits an X-ray beam 4B that is directed at a first test zone 10 containing a sample of Uranium Hexafluoride (UF6) 22 in its interior chamber 12. However, the X-ray beam 4B is also directed at a second test zone 11 which holds a vacuum in its interior chamber 13 for the purposes of calculating the attenuation of the second test zone 11, which second test zone 11 is provided adjacent the first container test zone 10. These two test zones 10, 11 should be oriented such that they experience similar heat temperature, humidity, and other conditions, other than the presence of UF6 in one and not the other. The greater the difference between their conditions, the greater the potential error calculating the enrichment of the Uranium. The same is true of their construction—substantially identical container test zones 10, 11 will result in more accurate data and more accurate calibrations. Preferably, the container test zones 10, 11 are placed immediately adjacent to one another such that their longitudinal axes are parallel substantially in the same direction, such that they are each impinged upon by a similar amount of X-rays at preferably substantially the same angle, and are substantially identical in construction.

The X-ray beam 4B is directed at the container test zones 10, 11 where a portion of the beam 4B passes through the first test zone 10 and the UF6 22 contained therein, and another portion of the beam 4B passes through the second test zone 11. As above, the second test zone 11 has only a vacuum, which is preferably only a fraction of the working pressure of the UF6 filled test zone 10 (and is more preferably less than 1/10 the working pressure), in its interior chamber 12, and so does not attenuate as many X-rays as does the first test zone 10 which contains UF6. A detector 16 measures the quantity of X-rays which pass through the first test zone 10 and the UF6 22 it contains, while a detector 17 measures the quantity of X-rays which pass through the container test zone 11. These detectors 16, 17 are preferably Thallium doped Sodium Iodide scintillating detectors, and it is noted that that they may operate simultaneously or sequentially, and that a single detector may be capable of detecting the X-rays passing through both test zones 10, 11.

The detectors 16, 17 are connected to a multi-channel analyzer 32 which sorts the pulses which are generated by the detectors 16, 17 when they detect X-rays. The multi-channel analyzer 32, as above, then creates a histogram of the X-ray pulse height distribution which was detected by the detectors 16, 17, and transmits this information to an output device 20 which is preferably a digital processor such as is found in a personal computer. The digital processor may be integrated into the multi-channel analyzer 32, or vice versa.

Thus, both the value of I, as well as an up-to-date value of $I_0(t)$ can be calculated any time a new Uranium enrichment measurement is needed, as opposed to a single $I_0(t)$ value which is typically used for months or years at a time in prior art systems, as it is costly and time consuming to take the system offline to perform recalibrations.

The system 30 may also utilize an X-ray stabilization loop (not shown), which would use the newly calculated $I_0(t)$ and a value for $I_0$set as the inputs to an integrator, which would control the output of the artificial X-ray source 2.

Figure 2:
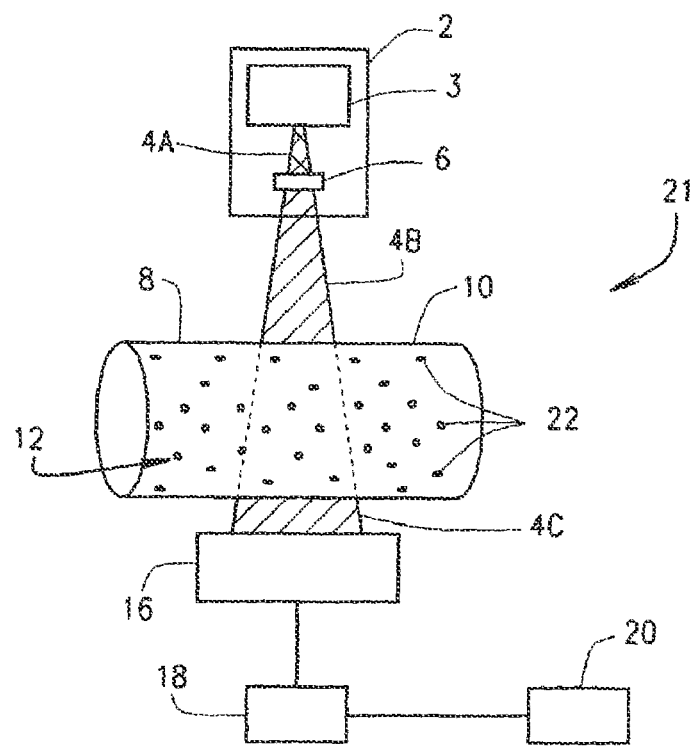
FIG. 2 is a schematic diagram of an embodiment of the present invention for measuring the attenuation of a container which contains UF6 gas.
Figure 4:
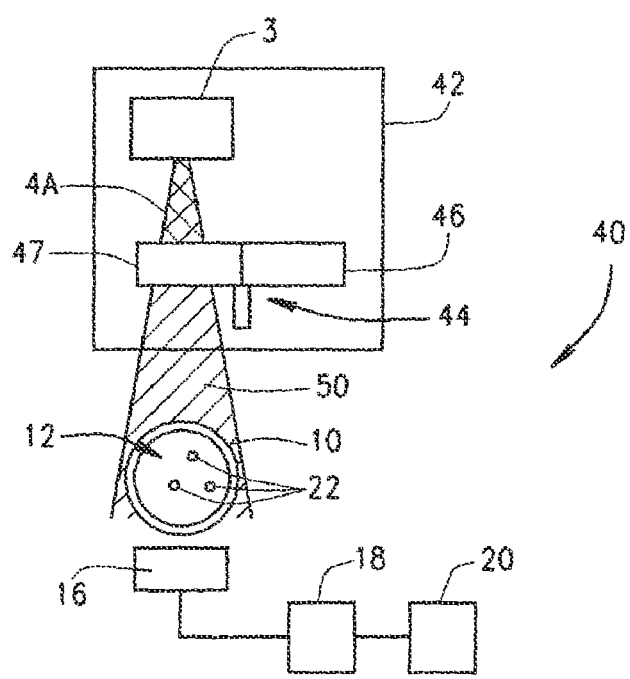
FIG. 4 is a schematic diagram of a preferred embodiment of the present invention including multiple X-ray filters.

FIG. 4 illustrates a preferred embodiment of a system 40 for measuring the $^{235}$U enrichment in UF6 gas. Unlike in the system 30 shown in FIG. 3, the system 40 in FIG. 4 does not use two test zones, and unlike the system 1 shown in FIGS. 1 and 2, does not use a baseline attenuation to be measured (or requires only a single instance of such calibration) prior to analyzing the Uranium content of UF6. An artificial X-ray source 42, which can preferably generate X-rays from 12 keV to 120 keV, includes an X-ray generation source 3 which emits a beam of X-rays 4A, and a drive assembly 44 on which a first filter 46 and a second filter 47 are mounted. The drive assembly 44 moves the filters sequentially in the path of the X-ray beam 4A by rotating the filters about an axis. Thus, depending on which filter 46, 47 the rotation assembly 44 has moved in the path of the X-ray beam 4A at that time, filtered X-ray beam 4B may contain X-rays of either of a first energy level or a second energy level. The angular velocity in revolutions per minute of the drive assembly 44 corresponds to the number of times the filtered X-ray beam would change from one energy level to the other and back.

It is noted that the filters 46, 47 need not be included inside the artificial X-ray source 42, but could instead be a separate component or separate components. It is further noted that an X-ray generation source 3 capable of emitting X-rays of substantially those energies desired, and capable of alternating between at least two desired energy levels could be used instead of filters 46 and 48 and rotation assembly 44. Further, more than two filters could be used if desired. Two separate X-ray sources could also be used. The X-ray beam 4 is preferably a "hard" X-ray beam with energy levels of between 12 keV and 120 keV, which have higher penetrating abilities than lower energy "soft" X-rays. However, if lower penetrating abilities are needed, "soft" X-rays could be used as above.

The first and second energy levels may be selected according to several different schemes. In a first scheme, the first and second energy levels are selected with a difference sufficient to produce distinct peaks, i.e., peaks which do not overlap when charted on a histogram. For example, a 22-keV line (preferably an Ag filter) and a 39-keV (preferably a Sm filter) provide the necessary sensitivity for measuring the attenuation because the 22-keV peak is distinct from the 39-keV peak when graphed, and therefore the ratio of the two peaks can be used to measure the attenuation of the UF6. Thus, two data sets can be separated from the output, where each data set contains the detected X-ray data for a single energy level. The density of the UF6 is then defined by the equation:

$$\rho_{UF6} = \frac{1}{(\mu_{UF6}^{Ag} - \mu_{UF6}^{Sm}) \cdot d_{UF6}} \cdot \ln\left(\frac{I_1^{Sm}}{I_1^{Ag}} \cdot \frac{\varepsilon_{Ag}}{\varepsilon_{Sm}} \cdot \exp\left[-\left(\mu_{Al}^{Ag} - \mu_{Al}^{Sm}\right) \cdot \rho_{Al} \cdot d_{Al}\right]\right)$$

where $\mu^{Ag}_{UF6}$, $\mu^{Sm}_{UF6}$, $\mu^{Ag}_{Al}$, and $\mu^{Sm}_{Al}$ are the mass attenuation coefficients, $I_1^{Sm}$ and $I_1^{Ag}$ are the intensity (count rate/unit of time) of the attenuated X-ray beam having passed through the container 8 test zone 10 and UF6, $\varepsilon_{Ag}$ and $\varepsilon_{Sm}$ are the conversion efficiencies for Ag and Sm K-alpha lines, $\rho_{Al}$ is the density of the container 8 test zone 10 wall, $d_{Al}$ is the thickness of this wall that the X-ray beam 4 preferably encounters, and $d_{UF6}$ is the thickness of the UF6. The sensitivity of a dual line densitometer may be reduced by up to approximately 25% compared to the sensitivity for the 22-keV line only, but allows for the compensation of instrument instability errors of the source and spectrometer. The spectral interferences are mitigated, allowing higher accuracy to be achieved.

The detector 16 is connected to a multi-channel analyzer 32 which sorts the pulses which are generated by the detector 16 when it detects the X-rays. The multi-channel analyzer 32 then creates a histogram of the X-rays energy levels which were detected by the detector 16, and transmits this information to an output device 20 which is preferably a digital processor as is typically found in a personal computer. The timing of the filter rotation is correlated to the output of the detector, such that the energy level of the X-rays detected by the detector 16 is known with regard to the output. Thus, measuring the attenuation of X-rays having two different energy levels allows for the density of UF6 in a sample to be calculated.

It is noted that the intensity of the two X-ray beams 4B having two differing energy levels may be substantially different. For example, in the case of a 100-mm internal diameter of the test zone 8 and an aluminum container 10 wall thickness of 5-mm, the attenuation for the 22 keV Ag k-line is approximately 250 times higher than for the 39 keV Sm k-line. Therefore, in order to have roughly equal measured rates, the Sm line incident the pipe would preferably be approximately 250 times lower than the Ag line.

In a second scheme, the energy levels are selected on the Uranium L-edge such that the mass attenuation coefficient ($\mu_{UF6}$) for Uranium at the first energy level is very different from the mass attenuation coefficient for Uranium at the second energy level, while the mass attenuation coefficient of Aluminum ($\mu_{Al}$), which preferably defines the test chamber, with aluminum alloys being preferred, at the first energy level is very similar to the mass attenuation coefficient of the Aluminum at the second energy level. Essentially: $(\mu_{UF6})_1$ is much greater or less than $(\mu_{UF6})_2$, while $(\mu_{Al})_1$ is approximately equal to $(\mu_{Al})_2$. Thus, Uranium's mass attenuation coefficient has a high sensitivity to the two energy levels while Aluminum's mass attenuation coefficient has a low sensitivity to the two energy levels, when the energy levels are chosen correctly. Preferably, the first filter 46 is such that the first energy output level is about 16.6-keV (preferably an Nb filter), and the second filter 47 is such that the second energy output level is about 17.5-keV (preferably a Mo filter). As an example, using these first and second energy levels at approximately 0.2 Torr pressure in the container, $\mu_{UF6}$ at the second energy level is approximately 63% higher than $\mu_{UF6}$ at the first energy level (approximately 75 cm$^2$/g versus approximately 46 cm$^2$/g), whereas $\mu_{Al}$ at the second energy level is approximately only 16% higher than $\mu_{Al}$ at the first energy level (6.1 cm$^2$/g versus 5.25 cm$^2$/g)—the percent difference in $\mu_{UF6}$ is approximately 4 times greater than that in $\mu_{Al}$ at these two energy levels. Preferably, the ratio between percent differences is at least 2/1, though higher ratios produce greater accuracy. Lower ratios are functional, though they tend to provide less accuracy.

The Aluminum in the container test zone 10 preferably attenuates the X-Rays of the first energy level similarly to the second energy level, while the UF6 22 preferably attenuates the X-Rays of the first energy level differently than the second energy level. The detector 16 is connected to a multi-channel analyzer 32 which sorts the pulses which are generated by the detector 16 when it detects the X-rays. The multi-channel analyzer 32 then creates a histogram of the X-rays energy levels which were detected by the detector 16, and transmits this information to an output device 20 which is preferably a digital processor as is typically found in a personal computer. The timing of the filter rotation is correlated to the output of the detector, such that the energy level of the X-rays detected by the detector 16 is known with regard to the output. Thus, measuring the attenuation of X-rays having two different energy levels allows for the density of UF6 in a sample to be calculated.

Additionally, other energy levels could be used so long as either Uranium or Aluminum has a high sensitivity to the two energy levels, while the other of the two has a low sensitivity to the two energy levels. For example, Uranium has a low sensitivity to energy levels of 16.6 keV and 26.3 keV, while Aluminum has a high sensitivity to the differences in the energy levels. It is noted that a composite filter could be used, though the energy levels are preferably selected such that the lower energy level does not interfere with the escape peak of the higher energy level—preferably, the lower energy level is in the valley between the higher energy level peak and an iodine escape peak, if one is present. Additionally, the larger the difference between the energy levels, the higher the sensitivity. It is also noted that when utilizing this second scheme, it is preferred that a one-time initial calibration of the system be performed, in which a third energy level is used which, when compared to either the first or second energy levels, results in a high sensitivity to Aluminum and a low sensitivity to Uranium. For example, when 16.6-keV is one of the energy levels, a third energy level may be approximately 26.3-keV (preferably an Sb filter).

Whether using the first or second scheme, the X-ray beam 4B is directed at the test zone 10 such that the X-ray beam 4B passes through the test zone 10 and the UF6 contained therein. As the rotation assembly 44 rotates, the X-ray beam 4B is comprised of X-rays having either the first or second energy level. A detector 16 measures the quantity of X-rays which pass through the test zone 10 and the UF6 it contains. This detector 16 is preferably a Thallium doped Sodium Iodide scintillating detector, as above.

A third scheme, in which only a single X-ray energy level is utilized, but which creates an effect similar to the use of a second energy level may also be utilized. In this case, the thickness of a filter, such as an Ag filter which produces an approximately 22-keV energy level, is selected to transmit a fraction of the Bremsstrahlung continuum. Because of the attenuation in the Aluminum container 10, the low energy portion of the continuum is suppressed, creating a Bremsstrahlung peak distinct from the first energy level peak, which Bremsstrahlung peak is preferably located at about 40-keV when the preferred Ag filter is utilized and properly sized. The Ag filter acts as a notch filter, cutting off the low energies of the Bremsstrahlung continuum, thus forming the higher energy Bremsstrahlung peak. There may be an iodine escape peak resulting from the scintillator crystals which typically occurs approximately 28-keV below the photopeak. Thus, it is preferable for the filter peak to fall between the iodine escape peak and the higher energy Bremsstrahlung peak. Thus, the filter peak and the Bremsstrahlung peak are distinct and discernable from one another, and it is these two peaks which are used to calculate the attenuation of the UF6. It is noted that this system is less accurate because of inherent spectral interference, but uses a simple configuration and a lower power tube. Thus, it may be suitable for so called "go/no go" applications where accuracy is not critical. This may be implemented when two lines are accumulated simultaneously by composite filter, and is not preferably implemented when the rotating dual filter setup is utilized.

Figure 5A:
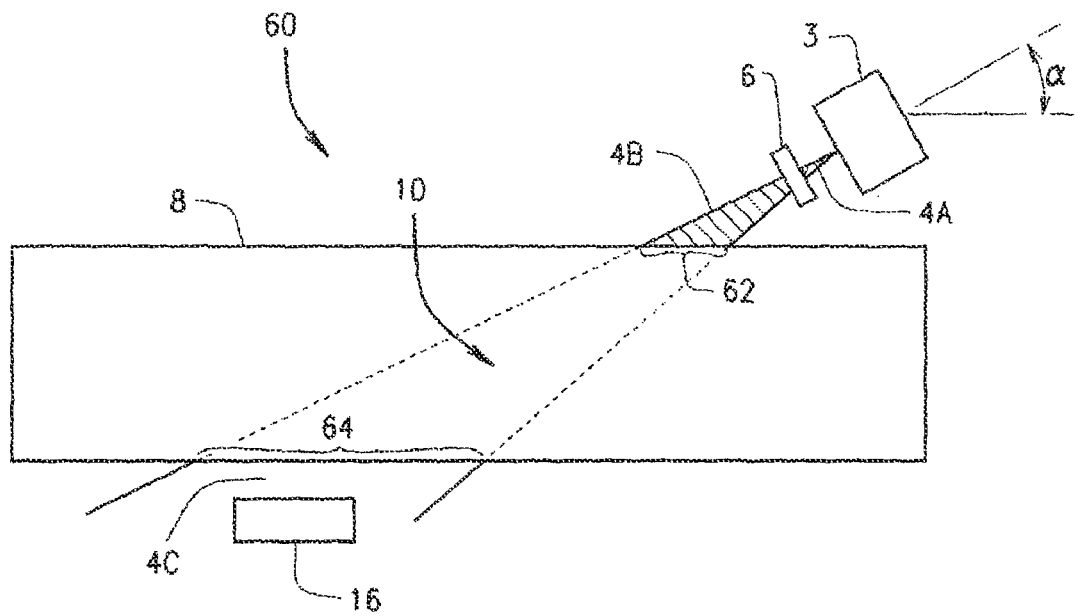
FIG. 5A is a plan view of an alternative configuration of an X-ray source, a container test zone and a detector according to an embodiment of the present invention.

Additionally, as the UF6 attenuation is proportional to the pressure and length over which the X-ray beam 4 passes through the UF6, detection sensitivity can be increased by increasing this length. The density of the UF6 in the test zone 10 may be low, the intensity of the 186 keV radiation emitted by $^{235}$U is typically low (1-2 counts per second). The background radiation due to Compton scattering of the surrounding Uranium material as well as the naturally accrued isotopes of Thorium and $^{40}$Potassium can overwhelm the information $^{235}$U radiation. Two alternative embodiments of a system 60 for determining the enrichment factor of $^{235}$U in UF6 is therefore illustrated in FIGS. 5A and 5B. In FIG. 5A, X-ray generator source 3 includes the same components as above, including filter 6.

The X-ray generator source 3 is disposed along the length of the container 8, and the beam 4B is directed through the test zone 10 at an acute angle α to the longitudinal axis of the test zone 10, which angle is preferably between about 10 degrees and about 80 degrees, as shown in FIG. 5A. The X-ray beam 4B emitted from the artificial X-ray source (not numbered) is directed at a container test zone 10 at angle α, which container 8 preferably includes an Aluminum pipe. The attenuated X-ray beam 4C is then detected by a detector 16 capable of measuring the quantity of X-rays passing through the test zone 10. The detector 16 is preferably a Thallium doped Sodium Iodide scintillating detector, and may be located within the path of the beam at second zone 64, as shown in FIG. 5A. This allows the X-ray beam 4B to pass through more UF6, thus heightening the detection capabilities of this geometry. The effective transmission thickness of the container 8 wall is equal to the thickness of the container walls divided by sin(α), while the effective transmission thickness of the UF6 is equal to the internal diameter of the container 8 divided by sin(α).

Figure 5B:
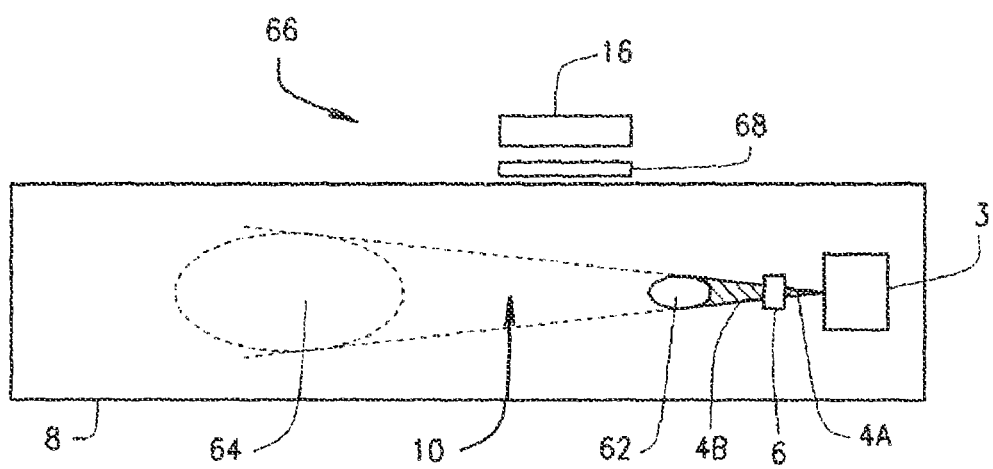
FIG. 5B is an elevation view of an alternative configuration of an X-ray source, a container test zone and a detector according to an embodiment of the present invention in which X-ray fluorescence is measured as opposed to X-ray transmission.
Figure 6:
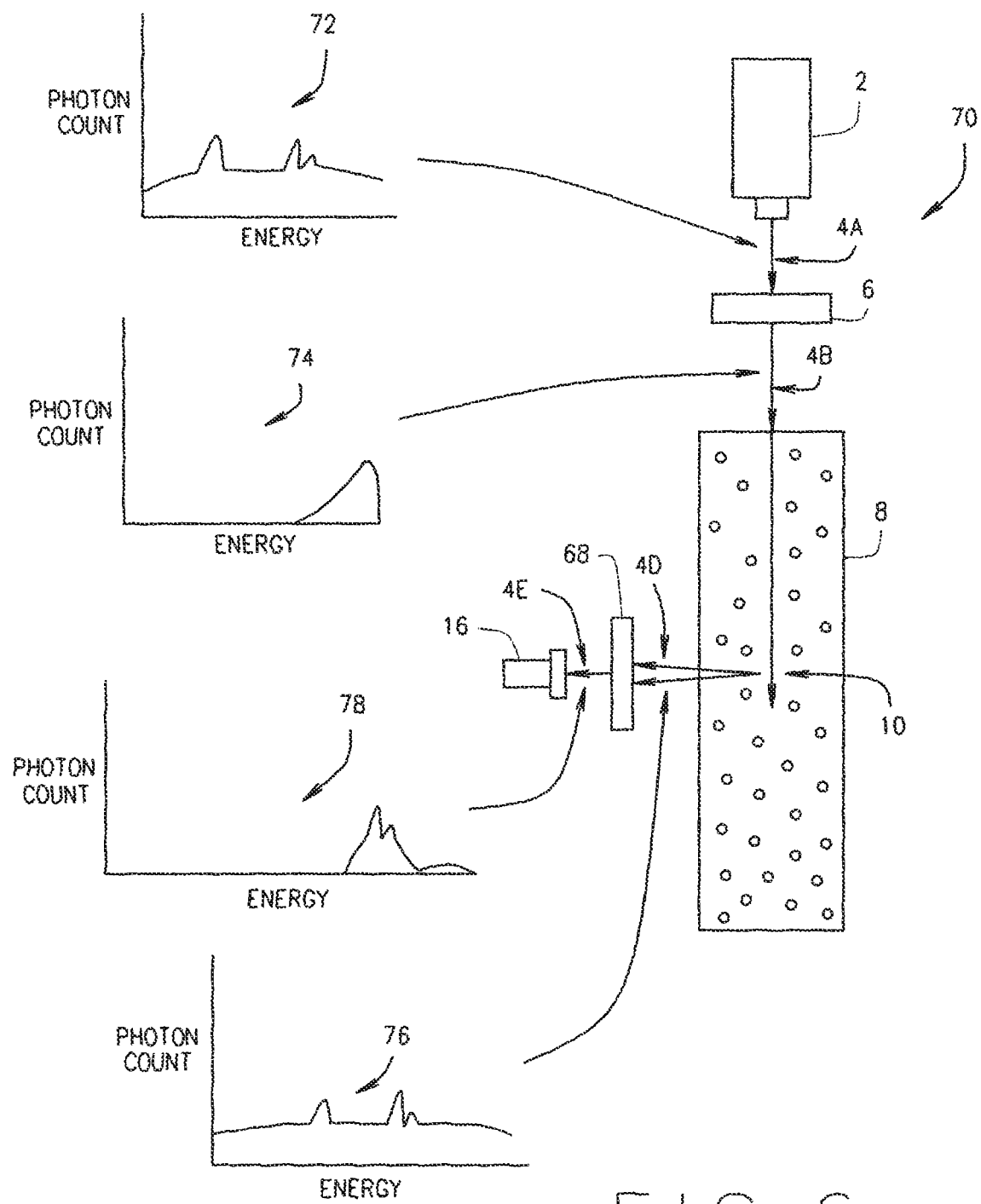
FIG. 6 is a schematic diagram of a preferred embodiment of the present invention utilizing X-ray Fluorescence to measure the enrichment of UF6, and including exemplary pulse height spectrums (which are not necessarily created in actual operation) at various locations along the system.

Alternatively, as is shown in the system 66 of FIG. 5B and FIG. 6, X-ray fluorescence may be used to calculate the $^{235}$U to Uranium enrichment factor. By measuring the fluorescent X-rays that are emitted by the UF6 (between approximately 94.7 keV and 98.4 keV) when an X-ray from X-ray beam 4 excites a UF6 molecule, the total amount of UF6 can be calculated. In the embodiments shown in FIGS. 5B and 6, filter 6 may be an absorber preferably made from a high "z" material (having a large number of protons) such as Rhenium, Tantalum, or Tungsten. As shown in FIG. 6, artificial X-ray source 2 outputs a spectrum of X-ray energy levels represented in FIG. 6 by graph 72. Filter 6 hardens the initial X-ray beam 4A by attenuating the X-rays below the approximately 115 keV absorption edge (a sharp discontinuity in the absorption spectrum of X-rays by an element that occurs when the energy of the photon corresponds to the sum energy of all shells of the atom) for Uranium, as shown by graph 74. The thickness and material of the filter 6 are selected so that the combined absorption with the container 8 wall provides increased absorption at the region of Uranium K-alpha lines (98.4 keV and 94.7 keV) and lessened suppression of the Bremsstrahlung continuum above the approximately 115 keV absorption edge of Uranium. In FIG. 5A, the X-ray generation source 3 is disposed along the length of the container 8, and the beam 4B is directed through the test zone 10 at an acute angle α to the longitudinal axis of the test zone 10, which angle is preferably between about 10 degrees and about 80 degrees. As is better seen in FIG. 5B, X-ray beam 4B intersects the test zone 10 at first wall zone 62, travels through the test zone 10 and UF6, and exits the test zone at second wall zone 64. Second wall zone 64 is larger than first wall zone 62 because of the widening of the beam 4B. As seen in FIG. 6, the artificial X-ray source 2 may be positioned at one end of the container 8 such that the X-ray beam 4 passes roughly straight through the test zone 10 and UF6.

The detector 16, which is preferably a phoswich scintillator, is preferably disposed along the test zone 10 outside container 8. Where the configuration of FIG. 5B is utilized, the phoswich scintillator is positioned between the first wall zone 62 and second wall zone 64 out of the path of X-ray beam 4, and preferably rotated about 90 degrees around the test zone 10 from the first and second wall zones 62, 64. By positioning the detector 16 out of the line of X-ray beam 4, the added radiation caused by the Compton scattering and backscattering from X-ray beam 4 impinging the container 8 walls can be largely avoided. As these fluorescent X-rays are of a much lower intensity than the transmitted X-rays, avoiding Compton scattering and backscattering is more important with this technique than in previously discussed techniques. Detector 16 may be oriented without rotating it about the test zone 10 from the first and second wall zones 62, 64 where said Compton scattering and backscattering are shielded. However, the configuration of FIG. 6 is preferred, because it avoids much of the scattering.

When a molecule of UF6 absorbs some of the energy from an X-ray, an electron in the K shell of the Uranium atom of the molecule of UF6 may be ejected from the atom. A higher energy electron (from the L or M shells) then jumps down to fill the vacancy left by the ejected electron, and emits a characteristic X-ray (K line) in the process. This leaves a void in the L or M shells, which would then, itself, be filled by a higher energy electron, which would emit another characteristic X-ray (L line) in the process. These characteristic X-rays then exit the container 8 and have an exemplary spectrum shown in histogram 76. They pass through another high-z filter (preferably a Thalium absorber) 68 which has an absorption edge of 109-keV, which suppressed the continuum above the Uranium X-rays. The X-rays which may then be detected by detector 16 have an exemplary spectrum shown in histogram 78. Detector 16 is also operable for counting the amount of background 186 keV radiation, and may additionally include a Thalium absorber 68 with an absorption edge of about 109 keV to suppress the continuum above the Uranium X-ray lines. Thus, the detector counts the 186 keV radiation as well as the 94.7 keV to 98.4 keV fluorescent X-rays, which allows for a determination of the enrichment of $^{235}$U in UF6.

It is noted that the X-ray Fluorescence system of FIGS. 5B and 6 may be used to measure UF6 density through a container 8 with an unknown thickness and wall material. Two measurements are taken: a transmission measurement of the attenuation through the test zone 10 and then through space without test zone 10. This is similar to the above dual measurements of the attenuation of the container 8 containing a vacuum and then containing UF6. Artificial X-ray source 2 remains from the above described embodiments, while filter 6 is preferably a Uranium filter such that approximately 94 and 98-keV X-rays are transmitted through test zone 10. A high-z filter 68 then filters the transmitted X-rays before detector 16 detects them. A similar procedure is executed in which no container 8 is present to attenuate the X-rays. From these two detected spectra, the attenuation of the container 8 can be calculated, and this attenuation is then used to correct for the attenuation of the exiting fluorescent X-rays when the fluorescent system is utilized.

One or more embodiments of the present invention provide for a system and method for calculating the $^{235}$Uranium content of Uranium Hexafluoride. An artificial X-ray generation source 2, or an X-ray synthesizer machine, which preferably utilizes an energetic electron process, is used to bombard a test zone 10 containing UF6 with X-rays of a specific energy level (or energy levels) to determine the enrichment of $^{235}$U in the test zone 10. An empty (vacuum) test zone 11 may be used to calculate a baseline attenuation of the X-rays, or X-rays of two different energy levels may be used to determine the attenuation of the Uranium Hexafluoride (UF6) alone. The quantity of $^{235}$Uranium can be calculated by measuring the 186 keV radiation which $^{235}$U spontaneously emits. These values allow for the calculation of the enrichment of $^{235}$U in Uranium Hexafluoride gas.

While particular elements, embodiments, and applications of the present invention have been shown and described, it is understood that the invention is not limited thereto because modifications may be made by those skilled in the art, particularly in light of the foregoing teachings. It is therefore contemplated by the appended claims to cover such modifications and incorporate those features which come within the spirit and scope of the invention.

What is claimed is:

1. A method for determining the proportional $^{235}$U content of UF6, the method comprising:
providing UF6 in a first container having a test zone;
measuring a quantity of radiation spontaneously emitted by $^{235}$U in said UF6;
generating X-rays of a first energy level in an X-Ray synthesizer machine;
irradiating at least a portion of said first container and said UF6 in said first container with said first energy X-ray, said first energy X-rays being directed at an acute angle to the longitudinal axis of said test zone;
measuring a quantity of X-rays exiting the first container and UF6; and
determining the fraction of $^{235}$U present in the UF6 relative to the total Uranium content of said UF6 utilizing the quantity of detected first energy X-rays transmitted through the container and UF6 and the $^{235}$U radiation count.

2. The method of claim 1 wherein said acute angle being between 10 degrees and 80 degrees.

3. The method of claim 2, further including:
positioning said detector along said first container test zone between a first zone where said first energy X-rays enter said test zone and a second zone where said first energy X-rays exit said test zone and rotated around said test zone by approximately 90 degrees from these zones.

4. The method of claim 2, further including:
hardening said first energy X-rays by positioning a first absorber being between said X-ray synthesizer machine and said test zone to attenuate the X-rays below approximately 115 keV.

5. The method of claim 2, further including:
suppressing the fluorescent X-rays above approximately 109 keV by positioning a second absorber between said detector and said test zone.

6. A system for determining the proportional $^{235}$U content of UF6, the system comprising:
a first ionizing radiation pervious container with a first test zone;
an X-Ray synthesizer machine disposed to direct a beam of first X-Rays of a first energy level through said first container test zone; and
a first detection device capable of measuring the quantity of radiation spontaneously emitted by $^{235}$U in a UF6, and capable of detecting a quantity of X-Rays exiting the first container test zone and any UF6 contained in said first container test zone.

7. The system of claim 6, further including:
a second ionizing radiation pervious container with a second test zone generally similar in construction to the first container test zone, where said second container test zone being positioned relative to the first container test zone such that the second container test zone experiences generally similar environmental conditions as the first container test zone apart from a lack of UF6 mixture in the second container test zone; and
a second detection device positioned to measure a quantity of first energy X-Rays being additionally transmitted through said second container, said first energy X-Rays being emitted by said X-Ray synthesizer machine, where said first detection device measuring the quantity of first energy X-rays being transmitted through said first container test zone and any UF6 contained in said first test zone.

8. The system of claim 7 wherein said X-Ray radiation source being additionally disposed to direct a beam of second X-Rays of a second energy level through said first container test zone,
where said detection device being positioned to detect the quantity of first and second X-Rays transmitted through the first container and UF6, and
where said determining means additionally for determining the enrichment of $^{235}$U in UF6 utilizing attenuation resulting from UF6 in the first container test zone apart from the attenuation resulting from the first container test zone.

9. The system of claim 8 wherein first container test zone having a low sensitivity to the difference between the first and second energy X-rays while UF6 having a high sensitivity to the difference between the first and second energy X-rays.

10. The system of claim 7, further including:

a first filter positioned between the X-ray synthesizer machine and the test zone to filter X-Ray radiation such that the first energy level being less than about 50 keV when said first energy X-rays first impinging the first container test zone; and a second filter position between the X-ray synthesizer machine and the test zone to filter X-Ray radiation such that the second energy level being less than about 50 keV and is not equal to the first energy level when said second energy X-rays first impinging the first container test zone.

11. The system of claim 10 wherein the first and second filters being mounted on a rotation assembly operable to sequentially move the first and second filters sequentially in line with the X-ray beam causing the first container test zone to be irradiated with X-rays of energy levels alternating between the first energy level and the second energy level.

12. The system of claim 10 wherein the first and second filters being assembled in a composite filter assembly operable to allow the first and second energy X-rays of the X-ray beam to at least partially pass through.

13. The system of claim 10 wherein the first energy level being about 16.6 keV and the second energy level being about 17.5 keV.

14. The system of claim 6, further including:
a first filter positioned between the emitted and the test zone to filter X-ray radiation such that the first energy level is less than about 50 keV when the X-ray radiation first impinging the first container test zone.

15. The system of claim 14 wherein said the first energy level being about 22 keV.

16. The system of claim 6, further including:
at least one first filter positioned between the emitted and the test zone to filter X-ray radiation such that the first energy level is less than about 50 keV when said first energy X-rays first impinging the first and second container test zones.

17. The system of claim 16 wherein the first energy level being about 22 keV.

18. The system of claim 6 wherein the first container test zone being elongate, and where said X-ray synthesizer machine being disposed along the first container test zone such that said X-ray beam being directed through said first container test zone at an acute angle to the longitudinal axis of said first container test zone.

19. The system of claim 18 wherein said acute angle being between 10 degrees and 80 degrees.

20. A method for measuring the $^{235}$U enrichment of UF6, the method comprising:
providing UF6 in a first container having an elongate test zone;
measuring the quantity of radiation spontaneously emitted by $^{235}$U in said UF6;
irradiating at least a portion of said first container and said UF6 in said first container with first and second energy X-rays;
measuring a quantity of first energy X-rays and a quantity of second energy X-rays exiting the first container and UF6; and
determining the fraction of $^{235}$U present in the UF6 mixture relative to the total Uranium content of said UF6 mixture utilizing the quantities of first and second energy X-rays transmitted through the container and UF6 mixture and the $^{235}$U radiation count.

* * * * *